United States Patent
Dwyer, Jr. et al.

(10) Patent No.: US 6,302,580 B1
(45) Date of Patent: Oct. 16, 2001

(54) APPARATUS FOR SOLID STATE DIGITAL IMAGER TRACKING RADIOGRAPHY

(75) Inventors: John E. Dwyer, Jr., Muskega; Jeffrey A. Kautzer, Waukesha; Thomas M. Leeds, Pewaukee, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/199,943

(22) Filed: Nov. 25, 1998

(51) Int. Cl.[7] .................................................. H05G 1/02
(52) U.S. Cl. ............................. 378/197; 378/196; 378/4; 378/205
(58) Field of Search .................................... 378/197, 117, 378/4, 189, 193, 196, 205, 98.8

(56) References Cited

U.S. PATENT DOCUMENTS

| | | | |
|---|---|---|---|
| 3,577,160 | * | 5/1971 | White ................................. 378/162 |
| 4,071,769 | * | 1/1978 | Brunnett et al. . | |
| 4,884,293 | * | 11/1989 | Koyama ............................. 378/197 |
| 5,572,567 | | 11/1996 | Khutoryansky et al. . | |
| 5,579,359 | | 11/1996 | Toth ................................. 378/19 |
| 5,636,259 | | 6/1997 | Khutoryansky et al. . | |
| 5,680,430 | | 10/1997 | Khutoryansky et al. . | |
| 5,734,694 | | 3/1998 | Khutoryansky et al. . | |
| 5,751,788 | | 5/1998 | Khutoryansky et al. . | |
| 5,768,336 | | 6/1998 | Khutoryansky et al. . | |
| 5,844,961 | * | 12/1998 | McEvoy et al. ................ 378/98.8 |
| 5,870,450 | * | 2/1999 | Khutoryansky et al. .......... 378/197 |
| 5,883,937 | * | 3/1999 | Schmitt ............................ 378/98.8 |
| 6,005,911 | * | 12/1999 | Cheung ............................ 378/98.8 |

FOREIGN PATENT DOCUMENTS

| | | |
|---|---|---|
| 196 50 528 A1 | 6/1997 | (DE) . |
| 0 453 174 A2 | 10/1991 | (EP) . |
| 0 861 631 A2 | 9/1998 | (EP) . |

* cited by examiner

Primary Examiner—Robert H. Kim
Assistant Examiner—Pamela R. Hobden
(74) Attorney, Agent, or Firm—McAndrews, Held & Malloy, Ltd.; Peter J. Vogel; Michael A. Dellapenna

(57) ABSTRACT

A radiographic imaging system including a solid state x-ray imager is disclosed. An x-ray tube is supported in a vertical x-ray tube support system alternately or in addition to a overhead angulating x-ray tube support system. A solid state x-ray imager is supported in a wall stand alternately or in addition to an angulating table stand. Associated sensors sense the position of the solid state x-ray imager, and a position controller adjusts the position of the x-ray tube such that the x-ray tube is positioned at the center of the solid state x-ray imager. Readout circuitry receives the analog image from the solid state x-ray imager and transmits the corresponding digital information to a digital processor for image creation or manipulation. The digital image may than be displayed on a digital imager acquisition and display system.

16 Claims, 2 Drawing Sheets

APPARATUS FOR SOLID STATE DIGITAL IMAGER TRACKING RADIOGRAPHY

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

The present invention generally relates to medical diagnosis imaging systems, and in particular to a radiographic x-ray projection imaging system employing a solid state x-ray imager.

Conventional thoracic imaging generally has been performed with x-ray projection imaging. Typically, a patient stands with his or her chest against a wall bucky system as an x-ray technologist positions the wall bucky system and an x-ray tube at an appropriate height before taking an x-ray image of the region of interest. Similarly, other common views, including cervical and lumbar spine, skull, sinus, shoulder, and abdomen, may be imaged with such a static positioning system.

Tomographic techniques, or body section radiography, may also be used to facilitate imaging of anatomical structures that may be obscured by adjacent structures. In such instances, the structures that interfere with the structure to be imaged can be "blurred out," leaving the structure of interest clearly in view for unobstructed imaging. One of the most common variants of tomography is that of linear tomography. In a linear tomographic examination, a patient lies on a table bucky that is moved horizontally in the opposite direction as the lateral motion of an x-ray tube suspended from a ceiling system. Simultaneous to this lateral movement, the x-ray tube rotates to keep the beam directed at the same anatomy throughout the imaging process.

Although universal systems currently exist which allow for conventional radiographic and linear tomographic x-ray examinations, these systems require a bucky apparatus that uses conventional x-ray film and oscillating anti-scatter grids. A radiographic imaging system, for example shown in U.S. Pat. No. 5,572,567 to Khutoryansky et. al., permits an x-ray technologist to choose either a conventional radiographic mode or a linear tomographic mode. However, a bucky apparatus and oscillating anti-scatter grids are necessary, resulting in a system which can be unreliable and susceptible to breakdown, as well as incurring the time and expense of conventional film development.

Additionally, a mechanical linkage between the x-ray tube and the imager is sometimes used in imaging systems, leading to inordinately time-consuming equipment installation, complexity, and mechanical unreliability. Moreover, in radiographic imaging systems without automatic alignment of the x-ray tube and the x-ray film, an x-ray technologist must manually align the imaging device (including the conventional film and the bucky) with the x-ray tube, resulting in imaging examinations that tend to be overly time-consuming.

A need, therefore, exists for an improved radiographic system which does not require a bucky apparatus or oscillating anti-scatter grids. A need also exists for an improved radiographic system that allows an x-ray technologist to perform efficient and effective imaging examinations without the need for mechanical linkages previously required to connect an x-ray tube to a bucky apparatus.

BRIEF SUMMARY OF THE INVENTION

One aspect of the invention is a radiographic imaging system which is capable of producing high quality x-ray images without the use of conventional film or oscillating anti-scatter grids.

Another feature of the invention is a radiographic imaging system employing a solid state x-ray imager.

Another characteristic of the invention is an increase in x-ray technologist productivity by providing a radiographic system with a servo motor subsystem to facilitate automatic tracking.

One further characteristic of the invention is ease of equipment installation by providing a radiographic imaging system that requires no mechanical linkage between the x-ray tube and the solid state x-ray imager.

One embodiment of the invention, which encompasses one or more of the above features, includes a solid state x-ray imager mounted inside a vertical support system (wall stand), or alternately, mounted horizontally beneath an angulating table support system (table stand). For wall stand applications, an x-ray tube is resident in a floor-mounted vertical x-ray tube support system, which includes an x-ray tube support positioning mechanism and position sensors capable of automatic vertical translation. Alternately, for table and wall stand applications, the x-ray tube may reside in an overhead angulating x-ray tube support system, which includes an x-ray tube support positioning mechanism and position sensors capable of automatic vertical and horizontal translations, as well as tube angulation motion in which the incident angle of emitting x-rays is automatically controlled.

The solid state x-ray imager may be moved manually or via an automatic servo-motor subsystem. For wall stand or static table stand exposures, a position controller senses the position of the solid state x-ray imager and automatically aligns the solid state x-ray imager and the x-ray tube such that, preferably, the center of the incident x-ray beam is positioned at the center of the solid state x-ray imager.

For linear tomographic table exposures, the position controller functions as described above with the exception that the solid state x-ray imager is moved automatically in a horizontal direction, while the x-ray tube is moved laterally in the opposite direction, the incident angle of the x-ray directed at the same anatomical point throughout the imaging process.

BRIEF DESCRIPTION OF THE SEVERAL DRAWINGS

DETAILED DESCRIPTION OF THE INVENTION

Figure 1:
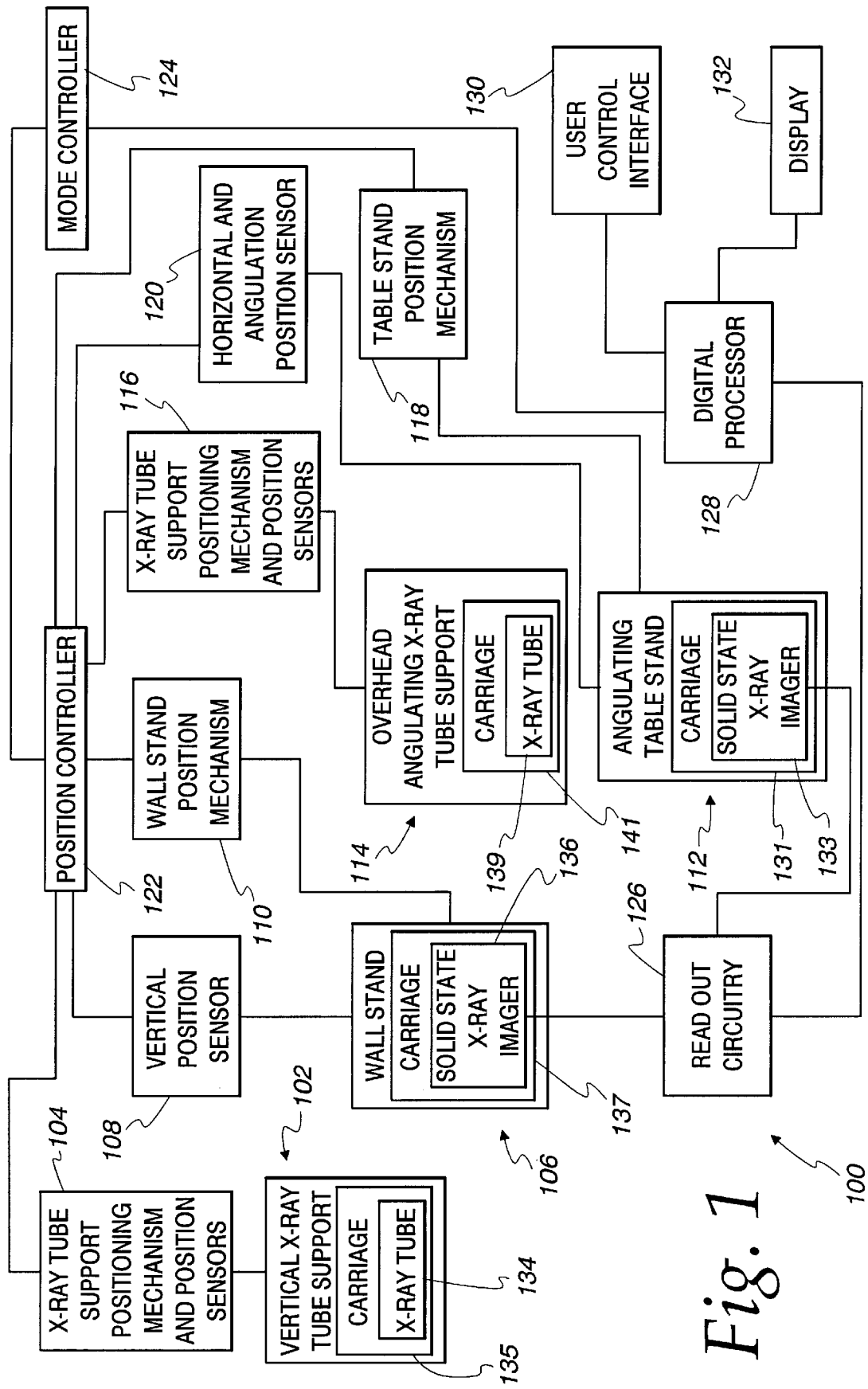
FIG. 1 illustrates a block diagram of a radiographic imaging system employing a solid state x-ray imager.

FIG. 1 shows a block diagram of a radiographic imaging system 100. The radiographic imaging system 100 includes a vertical x-ray tube support system 102, an x-ray tube support positioning mechanism and position sensors 104, a wall stand 106, a vertical position sensor 108, and a wall stand position mechanism 110. The radiographic imaging system 100 further includes an angulating table stand 112, an overhead angulating x-ray tube support system 114, an x-ray tube support positioning mechanism and position sensors 116, a table stand position mechanism 118, and a horizontal and angulation position sensor 120. The radiographic imaging system 110 also includes a position controller 122, a mode controller 124, readout circuitry 126, a digital processor 128, a user control interface 130, and a digital imager acquisition and display system 132.

A vertical x-ray tube support system 102 supports an x-ray tube 134 and is connected to an x-ray tube support positioning mechanism and position sensors 104. The output of the x-ray tube support positioning mechanism and position sensors 104 is connected to the position controller 122. Alternately or in addition, an overhead angulating x-ray tube support system 114 supports the x-ray tube 139 and is connected to an x-ray tube support positioning mechanism and position sensors 116. The output of the x-ray tube support positioning mechanism and position sensors 116 is connected to the position controller 122.

The wall stand 106 supports a solid state x-ray imager 136 and is connected to a vertical position sensor 108 and a wall stand position mechanism 110. The solid state x-ray imager 136 is available, for example, from General Electric Medical Systems, Waukesha, Wis. 53188. The output of the vertical position sensor 108 and the input to the wall stand position mechanism 110 are connected to the position controller 122. Similarly, the angulating table stand 112 supports the sold state x-ray imager 133 and is connected to a table stand position mechanism 118 and a horizontal and angulation position sensor 120. The input to the table stand position mechanism 118 and the output of the horizontal and angulation position sensor 120 are connected to the position controller 122.

A mode controller 124, user control interface 130, and digital imager acquisition and display system 132, are connected to and controlled by a digital processor 128. The readout circuitry 126 receives inputs from the solid state x-ray imager 136 resident in the wall stand 106 and/or the angulating table stand 112. The output from the readout circuitry 126, in turn, is connected to the digital processor 128.

For vertically-oriented imaging, the x-ray tube 134 in the vertical x-ray tube support system 102 generates imaging x-rays. The vertical x-ray tube support system 102 includes an x-ray carriage 135 which is movable vertically along the vertical x-ray tube support system 102, which supports the x-ray tube 134. A patient stands alongside the wall stand 106 with the portion of his or her body to be imaged in contact with the solid state x-ray imager 136 resident on the wall stand 106. The wall stand 106 includes an imager carriage 137 which is movable along the wall stand 106, and which supports the solid state x-ray imager 136. Movement of the solid state x-ray imager 136 along the wall stand 106 is achieved using the wall stand position mechanism 110. The x-ray carriage 135 and the imager carriage 137 may be mounted, for example, on bearings with a counterweight such that the carriage easily translates in the vertical or horizontal direction.

The vertical position sensor 108 is coupled to the wall stand 106 and includes an imager position output which represents the location of the solid state x-ray imager 136. The x-ray tube support positioning mechanism and position sensors 104 are coupled to the vertical x-ray tube support system 102 and include an x-ray tube position output which represents the location of the x-ray tube 134. The output of the x-ray tube support positioning mechanism and position sensors 104 and the output of the vertical position sensor 108 are connected to the position controller 122.

The position controller 122 may, in turn, automatically adjust the position of the x-ray tube 134 to correspond with the position of the solid state imager 136. The alignment may be performed, for example, using a servo-motor subsystem (not shown). The servo-motor subsystem is coupled to the x-ray position control output for automatic movement of the x-ray tube 134. Alternately, the alignment of the x-ray tube 134 to the solid state x-ray imager 136 may be performed by manual adjustment. The x-ray position control output aligns the x-ray tube 134 so that the x-ray beam is positioned to create exposures on the solid state x-ray imager 136. As a result, some x-rays will be detected by the solid state x-ray imager 136 which is preferably centered with respect to the x-ray tube 134.

Similarly, for horizontal imaging, the x-ray tube 139 in the overhead angulating x-ray tube support system 114 generates imaging x-rays. The overhead angulating x-ray tube support system 114 may be ceiling mounted, and provides automatic vertical and horizontal translations, as well as tube angulation motion in which the incident angle of emitting x-rays is automatically controlled. The overhead angulating x-ray tube support system 114 includes an x-ray carriage 141 which is movable horizontally along the overhead angulating x-ray tube support system 114, and which supports the x-ray tube 139. A patient lies on the angulating table stand 112 with the portion of his or her body to be imaged above the solid state x-ray imager 133 residing beneath the table. The angulating table stand 112 includes an imager carriage 131 which is movable along the angulating table stand 112, and which supports the solid state x-ray imager 133. Movement of the solid state x-ray imager 133 along the angulating table stand 112 is achieved using the table stand position mechanism 118. The x-ray carriage 141 and the imager carriage 131 may be mounted, for example, on bearings with a counterweight such that the carriage easily translates in the vertical or horizontal direction.

The horizontal and angulation position sensor 120 is coupled to the angulating table stand 112 and includes an imager position output which represents the differential or absolute location of the solid state x-ray imager 133. The x-ray tube support positioning mechanism and position sensors 116 are coupled to the x-ray tube carriage 41 and include an x-ray tube position output which represents the differential or absolute location of the x-ray tube 139. The output of the x-ray tube support positioning mechanism and position sensors 116 and the output of the horizontal and angulation position sensor 120 are connected to the position controller 122. The position controller 122, in turn, adjusts the position of the x-ray tube 139 to correspond with the position of the solid state imager 133. The alignment may be performed using a servo-motor subsystem (not shown). The servo-motor subsystem is coupled to the x-ray position control output for automatic movement of the x-ray tube 139. Alternately, the alignment of the x-ray tube 139 to the solid state x-ray imager 133 may be performed by manual adjustment. The x-ray position control output aligns the x-ray tube 139 so that the x-ray beam is positioned to create exposures on the solid state x-ray imager 133. As a result, some x-rays will be detected by the solid state x-ray imager 133 which is preferably centered with respect to the x-ray tube 139.

After an x-ray technologist determines whether a vertical or a horizontal image is to be made, the x-ray technologist may use a mode controller 124 to select a single exposure or an exposure sequence. The readout circuitry 126 converts analog image data from the solid state x-ray imager 133 to digital data and passes the digital data to the digital processor 128. The digital processor 128, in turn, reads the image received from the readout circuitry 126 and presents the data in visual form via a digital imager acquisition and display system 132. The digital imager acquisition and display system 132 displays the digital image received from the digital processor 128. A user may view the digital image displayed by the digital imager acquisition and display system 132 through a user control interface 130 that, for example, provides sophisticated image processing capabilities.

Figure 2:
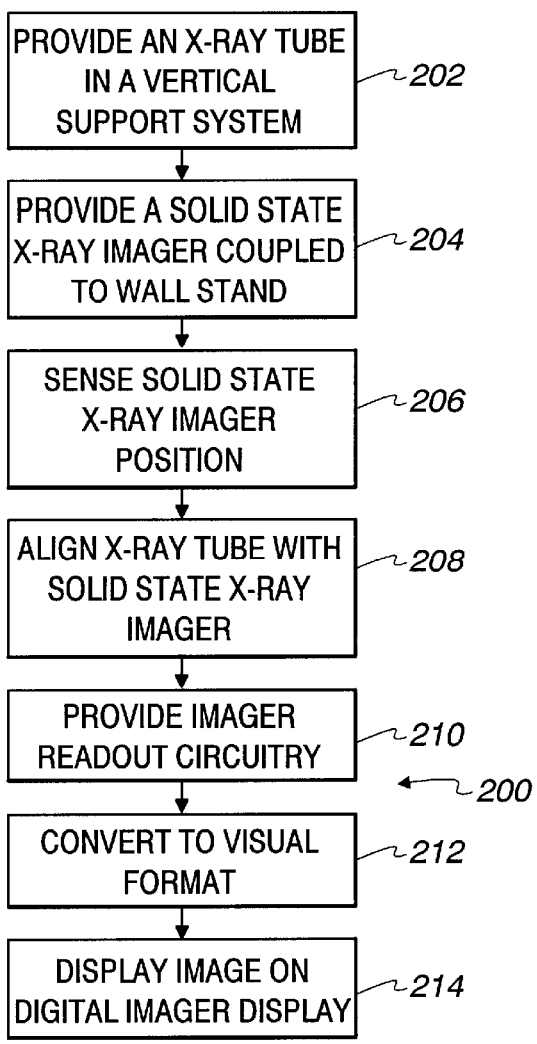
FIG. 2 illustrates a flow diagram of the imaging process in a radiographic imaging system (vertical orientation) employing a solid state x-ray imager.
Figure 3:
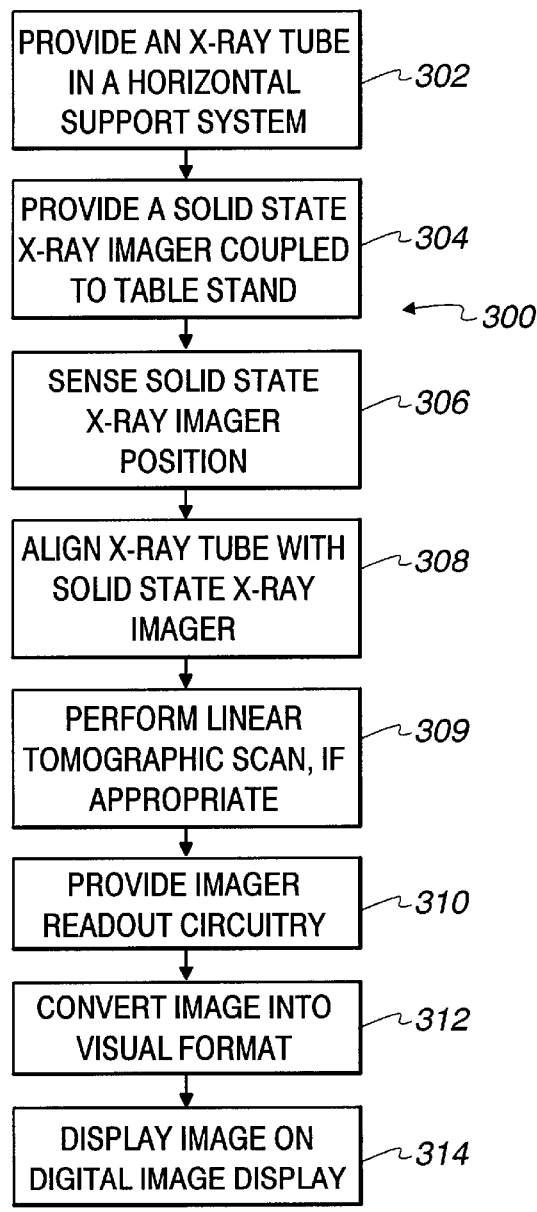
FIG. 3 illustrates a flow diagram of the imaging process in a radiographic imaging system (horizontal orientation) employing a solid state x-ray imager.

FIG. 2 and FIG. 3 supplement the discussion above with respect to FIG. 1. FIG. 2 shows a flow diagram 200 of the imaging process in a radiographic imaging system 100 (vertical orientation) employing a solid state x-ray imager 136. The method includes an x-ray tube provisioning step 202, a solid state x-ray imager provisioning step 204, a sensing step 206, an aligning step 208, a readout circuitry provisioning step 210, a converting step 212, and a displaying step 214.

Referring to FIG. 2, an x-ray tube 134 is provided at step 202 in a vertical x-ray tube support system 102. Next, a solid state x-ray imager 136 is provided at step 204 which is supported by an imager carriage 137 connected to a wall stand 106.

At the sensing step 206, a vertical position sensor 108 senses the position of the solid state x-ray imager 136. Similarly, an x-ray tube support positioning mechanism and position sensors 104 sense the position of the x-ray tube 134. Subsequently, at the aligning step 208, the position controller 122 adjusts the position of the x-ray tube 134 in correspondence to the position of the solid state x-ray imager such that the x-ray tube 134 is directed toward the center of the solid state x-ray imager 136.

At step 210, readout circuitry 126 is provided and receives the created image from the solid state x-ray imager 136 in analog form. The readout circuitry 126 then passes the analog image (or, preferably the digital form of the analog image) to the digital processor 128. At the converting step 212, the digital processor 128 receives the analog image from the readout circuitry 126 and converts the image into a visual format for display to the user at the displaying step 214.

Similarly, FIG. 3 shows a flow diagram 300 of the imaging process in a radiographic imaging system 100 (horizontal orientation) employing a solid state x-ray imager 133. The method includes an x-ray tube provisioning step 302, a solid state x-ray imager provisioning step 304, a sensing step 306, an aligning step 308, a readout circuitry provisioning step 310, a converting step 312, and a displaying step 314. If a linear tomographic image is selected, the method also includes a linear tomographic scanning step 309.

Referring to FIG. 3, an x-ray tube 139 is provided at step 302 in a overhead angulating x-ray tube support system 114. Next, a solid state x-ray imager 133 is provided at step 304 is supported by an imager carriage 131 connected to an angulating table stand 112.

At the sensing step 306, a horizontal and angulation position sensor 120 senses the position of the solid state x-ray imager 133. Similarly, an x-ray tube support positioning mechanism and position sensors 116 sense the position of the x-ray tube 139. Subsequently, at the aligning step 308, the position controller 122 adjusts the position of the x-ray tube 139 in correspondence to the position of the solid state x-ray imager 133 such that the x-ray tube 139 is directed toward the center of the solid state x-ray imager 133.

If selected by the x-ray technologist, a linear tomographic scan is performed at step 309 in lieu of a static table exposure. For linear tomographic table exposures, the position controller 122 functions as described above, that is, the position controller 122 adjusts the position of the x-ray tube 139 in correspondence to the position of the solid state x-ray imager 133. However, in the case of linear tomographic table exposures, the solid state x-ray imager 133 is automatically moved in a horizontal direction while the x-ray tube is moved laterally in the opposite direction with the incident angle of the x-ray directed at the same anatomical point in the patient throughout the imaging process.

Referring again to FIG. 3, at step 310, readout circuitry 126 is provided and receives the created image from the solid state x-ray imager 133 in analog form. The readout circuitry 126 then passes the analog image (or, preferably the digital form of the analog image) to the digital processor 128. At the converting step 312, the digital processor 128 receives the analog image from the readout circuitry 126 and converts the image into a visual format for display to the user at the displaying step 314.

While particular embodiments of the invention have been shown, it will be understood, of course, that the invention is not limited thereto since modifications may be made by those skilled in the art, particularly in light of the foregoing teachings. It is, therefore, contemplated by the appended claims to cover any such modifications an incorporate those features which constitute the essential features of these improvements within the true spirit and the scope of the invention.

What is claimed is:

1. A radiographic imaging system for generating medical diagnostic images, the radiographic imaging system comprising:

a first x-ray tube for generating and transmitting imaging x-rays;

an overhead angulating x-ray tube support system for said first x-ray tube, said support including an x-ray carriage movable along said support and supporting said first x-ray tube;

a first solid state x-ray imager for absorbing said x-rays generated by said first x-ray tube;

an angulating table stand for said first solid state x-ray imager including an imager carriage movable along said angulating table stand and supporting said first solid state x-ray imager;

a horizontal and angulation position sensor coupled to said angulating table stand and including an imager position output representative of a position of said first solid state x-ray imager;

a first position controller coupled to the imager position output, the position controller including a first x-ray position control output for adjusting the position of said first x-ray tube in correspondence with said first solid state x-ray imager position;

a second x-ray tube for generating and transmitting imaging x-rays;

a second solid state x-ray imager for absorbing said x-rays generated by said second x-ray tube;

a vertical x-ray tube support system for said second x-ray tube, said support including an x-ray carriage movable along said support and supporting said second x-ray tube for transmitting imaging x-rays toward said second solid state x-ray imager without moving said angulating table stand;

readout circuitry including an imager input connected to said first and second solid state x-ray imagers and a digital image output connected to a digital processor;

a wall stand for said second solid state x-ray imager including an imager carriage movable along said wall stand and supporting said second solid state x-ray imager;

a vertical position sensor coupled to said wall stand and including an imager position output representative of a position of said second solid state x-ray imager; and a second position controller coupled to the imager position output, the position controller including a second x-ray position control output for adjusting the position of said second x-ray tube in correspondence with said second solid state x-ray imager position without moving said table stand.

2. The radiographic imaging system of claim 1 wherein said imager carriage is adapted to allow manual adjustment of said second solid state x-ray imager.

3. The radiographic imaging system of claim 1 further comprising a servo-motor subsystem coupled to said second x-ray position control output for moving said second x-ray tube.

4. The radiographic imaging system of claim 3 wherein said second x-ray position control output aligns said second x-ray tube to the center of said second solid state x-ray imager.

5. The radiographic imaging system of claim 1 further comprising a digital imager acquisition and display system coupled to said readout circuitry for receiving and displaying an image acquired on said second solid state x-ray imager.

6. The radiographic imaging system of claim 1 wherein said imager carriage is adapted to allow manual adjustment of said first solid state x-ray imager.

7. The radiographic imaging system of claim 1 further comprising a servo-motor subsystem coupled to said first x-ray position control output for moving said first x-ray tube.

8. The radiographic imaging system of claim 7 wherein said control output aligns said first x-ray tube to the center of said first solid state x-ray imager.

9. The radiographic imaging system of claim 1 further comprising a digital imager acquisition and display system coupled to said readout circuitry for receiving and displaying an image acquired on said first and second solid state x-ray imagers.

10. A method for radiographic imaging, the method comprising:

providing a first x-ray tube within an overhead angulating x-ray tube support system;

providing a first solid state x-ray imager supported by an imager carriage connected to an angulating table stand;

sensing the position of said first solid state x-ray imager;

aligning said first x-ray tube relative to said solid state x-ray imager such that said first x-ray tube is positioned to create exposures on said first solid state x-ray imager;

providing a second solid state x-ray imager supported by an imager carriage connected to a wall stand;

providing a second x-ray tube within a vertical x-ray tube support system arranged to transmit x-rays from said second x-ray tube without moving said angulating table stand;

sensing the position of said second solid state x-ray imager;

aligning said second x-ray tube relative to said second solid state x-ray imager such that said second x-ray tube is positioned to create exposures on said second solid state x-ray imager without moving said angulating table stand; and reading images from said first and second solid state x-ray imagers and transferring said images to a digital processor.

11. The method of claim 10 wherein said step of aligning said second x-ray tube relative to said second solid state x-ray imager comprises positioning said second x-ray tube at the center of said second solid state x-ray imager.

12. The method of claim 10 further comprising the step of providing a linear tomographic mode comprising automatically moving said first solid state x-ray imager in a horizontal direction and concurrently moving said first x-ray tube in a longitudinal direction, opposite to that of said first solid state x-ray imager.

13. The method of claim 12 wherein the incident angle of the x-ray from the first x-ray tube is directed at the same anatomical point in a patient throughout the imaging process.

14. The method of claim 10 further comprising the step of converting said images to a digital image before the transferring step.

15. The method of claim 14 further comprising the step of displaying said digital images.

16. The method of claim 10 wherein said step of aligning said first x-ray tube relative to said first solid state x-ray imager comprises positioning said first x-ray tube at the center of said first solid state x-ray imager.

* * * * *